(12) United States Patent
Ting et al.

(10) Patent No.: US 9,064,039 B2
(45) Date of Patent: Jun. 23, 2015

(54) SYSTEM, METHOD AND RECORDING MEDIUM FOR CALCULATING PHYSIOLOGICAL INDEX

(75) Inventors: Chuan-Wei Ting, Kaohsiung (TW); Ching-Yao Wang, Tainan (TW)

(73) Assignee: Industrial Technology Research Institute, Hsinchu (TW)

(*) Notice: Subject to any disclaimer, the term of this patent is extended or adjusted under 35 U.S.C. 154(b) by 207 days.

(21) Appl. No.: 13/452,947

(22) Filed: Apr. 23, 2012

(65) Prior Publication Data

US 2012/0323131 A1 Dec. 20, 2012

Related U.S. Application Data

(60) Provisional application No. 61/497,965, filed on Jun. 17, 2011.

(30) Foreign Application Priority Data

Dec. 15, 2011 (TW) .............................. 100146537 A

(51) Int. Cl.
*A61B 5/0452* (2006.01)
*G06F 19/00* (2011.01)

(52) U.S. Cl.
CPC .......... *G06F 19/3431* (2013.01); *G06F 19/322* (2013.01)

(58) Field of Classification Search
USPC ................. 600/513, 515, 519, 523, 529, 544
See application file for complete search history.

(56) References Cited

U.S. PATENT DOCUMENTS

| 7,882,167 B2* | 2/2011 | Goldberger et al. .......... 709/200 |
| 8,475,387 B2* | 7/2013 | Derchak et al. .............. 600/529 |
| 2006/0189875 A1* | 8/2006 | Goldberger et al. .......... 600/513 |
| 2007/0066906 A1* | 3/2007 | Goldberger et al. .......... 600/509 |
| 2008/0045815 A1* | 2/2008 | Derchak et al. .............. 600/301 |
| 2009/0030762 A1 | 1/2009 | Lee et al. |
| 2009/0094627 A1 | 4/2009 | Lee et al. |
| 2009/0192394 A1* | 7/2009 | Guttag et al. ................. 600/509 |
| 2009/0271729 A1 | 10/2009 | Killoren Clark et al. |
| 2009/0275853 A1* | 11/2009 | Sarkela ........................ 600/544 |

(Continued)

FOREIGN PATENT DOCUMENTS

CN 1567331 1/2005

OTHER PUBLICATIONS

Pan et al., "Fast computation of sample entropy and approximate entropy in biomedicine," Computer Method and Programs in Biomedicine 104, 2011, pp. 382-396.

(Continued)

*Primary Examiner* — Christopher D Koharski
*Assistant Examiner* — Jeremiah Kimball
(74) *Attorney, Agent, or Firm* — Jianq Chyun IP Office

(57) ABSTRACT

A system, a method and a recording medium for calculating a physiological index are provided. The method includes: dividing a physiological data sequence into a plurality of windows; analyzing a data segment in each window to obtain metadata that represents data characteristics of the data segment; updating the metadata including the data characteristics of all data segments in the windows up to a previous window by using the metadata corresponding to one of the windows to obtain the metadata including the data characteristics of all data segments in the windows up to a current window; and finally, calculating the physiological index by using the updated metadata.

14 Claims, 14 Drawing Sheets

(56) References Cited

U.S. PATENT DOCUMENTS

2010/0324436 A1*  12/2010  Moorman et al. ............ 600/515
2013/0127845 A1    5/2013  Schauf
2013/0178731 A1*   7/2013  Bosl, William J. ........... 600/409

OTHER PUBLICATIONS

Vargas et al, "Multiscale entropy analysis of electroseismic time series," Natural Hazards and Earth System Sciences 8, 2008, pp. 855-860.

Sugisaki et al, "Online estimation of complexity using variable forgetting factor," Proceedings of the SICE Annual Conference, 2007, pp. 1-6.

Costa et al., "Multiscale Entropy Analysis of Complex Physiologic Time Series," Physical Review Letters 89 (6), Aug. 5, 2002, pp. 068102-1-068102-4.

Costa et al., "Multiscale entropy analysis of biological signals," Physical Review E 71, 2005, pp. 021906-1-021906-18.

Costa et al., "Multiscale Analysis of Heart Rate Dynamics: Entropy and Time Irreversibility Measures," Cardiovascular Engineering 8 (2), 2008, pp. 88-93.

Nikulin et al., "Comments on Multiscale Entropy Analysis of Complex Physiologic Time Series," Physical Review Letters 92 (8), Feb. 27, 2004, pp. 089803-1.

Pan et al., "Efficient Computation of Multiscale Entropy in Biomedicine," 2010 International Symposium on Computer, Communication, Control and Automation, 2010, pp. 49-52.

Pan et al., "Computing Multiscale Entropy With Orthogonal Range Search," Journal of Marine Science and Technology 19 (1), 2011, pp. 107-113.

Valencia et al., "Refined Multiscale Entropy: Application to 24-h Holter Recordings of Heart Period Variability in Healthy and Aortic Stenosis Subjects," Transactions on Biomedical Engineering 56 (9), Sep. 2009, pp. 2202-2213.

"Office Action of Taiwan Counterpart Application", issued on Jun. 9, 2014, p. 1-p. 6.

* cited by examiner $\tau = 2$ $x_1 x_2 x_3 x_4 x_5 x_6 x_7 x_8 \quad \cdots \quad x_i x_{i+1}$ $\square \quad \square \quad \square \quad \square \quad \cdots \quad \square$ $v_1 \quad v_2 \quad v_3 \quad v_4 \quad \cdots \quad v_j = \dfrac{x_i + x_{i+1}}{2}$ (a)

$\tau = 3$ $x_1 x_2 x_3 \, x_4 x_5 x_6 \, x_7 x_8 x_9 \quad \cdots \quad x_i x_{i+1} x_{i+2}$ $\square \quad \square \quad \square \quad \cdots \quad \square$ $v_1' \quad v_2' \quad v_3' \quad \cdots \quad v_j' = \dfrac{x_i + x_{i+1} + x_{i+2}}{3}$ (b)

FIG. 3

SYSTEM, METHOD AND RECORDING MEDIUM FOR CALCULATING PHYSIOLOGICAL INDEX

CROSS-REFERENCE TO RELATED APPLICATION

This application claims the priority benefits of U.S. provisional application Ser. No. 61/497,965, filed on Jun. 17, 2011 and Taiwan application serial no. 100146537, filed on Dec. 15, 2011. The entirety of each of the above-mentioned patent applications is hereby incorporated by reference herein and made a part of this specification.

BACKGROUND

1. Technical Field

The disclosure relates to a system, a method and a recording medium for calculating a physiological index.

2. Related Art

Using information technology to collect various physiological signals and analyze physiological heath status of an individual case is a joint collaborative research topic for the fields of medical care and information science. For example, analysis of an electrocardiogram (ECG) signal has been a very important issue in analysis of cardiovascular-related diseases, because it can directly reflect the status of heart function.

Most signs of diseases will show slight differences in the variability of operation and rhythm of physical organs, although many international companies and medical researchers have provided processes and methods for monitoring and analyzing the physiological signal, there are still some technical problems to be solved.

Taking the ECG as an example, current heart function examination mainly uses short-term ECG analysis. As many diseases cannot be detected from short-term ECG, researchers have developed physiological indexes that are mainly obtained by analyzing the complexity of the heart rhythm from the multi-scale perspective using long-term ECG in recent years. It is verified in researches that this type of indexes can exactly reflect the health status of the heart function. Calculation of multi-scale physiological index is more complex than the conventional statistical analysis of time-frequency domain, especially the effectiveness of multi-scale entropy (MSE) based on entropy has been proven in medical researches.

Although the long-term ECG analysis can provide complete physiological information of an individual case, the system needs a large space for storing long-term ECG data. How to design a new mechanism that can efficiently store the ECG information while calculating a long-term ECG physiological index is one of the challenges in long-term ECG analysis.

The long-term physiological index that is developed based on multiple scales can present a physiological state of an individual case in a long-term range, but the difference of the physiological state cannot be obtained through analysis of a short-term physiological signal. However, due to a considerable computation time, the application of long-term physiological index is restricted in interpretation of and research of symptoms after an individual case is attacked, and is not applied in monitoring and early warning of a physiological state of an individual case. It can be seen that, how to enable this type of multi-scale physiological indexes to have the capability of monitoring and evaluating the physiological state of an individual case in real time as far as possible is a very important issue in physiological monitoring of an individual case in clinic.

SUMMARY

The disclosure is directed to a system, a method and a recording medium for calculating a physiological index.

A method for calculating a physiological index is introduced herein, which is applicable in an electronic device. The method includes: dividing a physiological data sequence into a plurality of windows, in which each window includes a data segment of the physiological data sequence; analyzing the data segment in each window to obtain metadata that represents data characteristics of the data segment; updating metadata including the data characteristics of all data segments in the windows up to a previous window by using the metadata corresponding to one of the windows to obtain the metadata including the data characteristics of all data segments in the windows up to a current window; and calculating a physiological index by using the updated metadata.

A system for calculating a physiological index is introduced herein, which includes a converter and a computer system. The converter is used for detecting a physiological data sequence. The computer system includes a transmission interface, at least one storage medium, and a processor. The transmission interface is connected to the converter and is used for receiving the physiological data sequence. The at least one storage medium is used for storing the physiological data sequence. The processor is coupled to the transmission interface and the at least one storage medium, and is used for dividing the physiological data sequence into a plurality of windows, and analyzing a data segment of the physiological data sequence in each window to obtain metadata that represents data characteristics of the data segment, updating metadata including the data characteristics of all data segments in the windows up to a previous window by using the metadata corresponding to one of the windows to obtain the metadata including the data characteristics of all data segments in the windows up to a current window; and calculating a physiological index by using the updated metadata.

A computer readable recording medium with a stored program is introduced herein, which can complete the method when the program is loaded on a computer and is executed.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

FIG. 3(a) and FIG. 3(b) show examples of a coarse-graining procedure according to an embodiment of the disclosure.

DETAILED DESCRIPTION OF DISCLOSED EMBODIMENTS

The disclosure provides a method for calculating a physiological index in long-term physiological data analysis, in which physiological data that gradually enters a system is divided into relative short physiological data segments by using the concept of the window, so as to solve the problem of low efficiency caused by a large amount of data in batch mode calculation. Additionally, as for the problem of storage space for long-term physiological data, an embodiment of the disclosure also provides a method for replacing originally stored physiological data with metadata characteristics, in which, when entering each window, information of metadata is updated to describe characteristics of all previous data. Finally, an embodiment of the disclosure provides a method for calculating a long-term physiological index through combination of systematic data structure and data of the metadata. Through the three processes mentioned above, the disclosure enables the system to provide a long-term physiological index, especially the multi-scale entropy (MSE) index that is the most complex in calculation in multi-scale analysis. An embodiment of the disclosure also provides data for health care workers, so that monitoring and analysis of a long-term physiological state can be widely adopted in clinical practice.

In the following embodiments, an ECG is described as an example, but the application of the disclosure is not limited to the ECG.

Figure 1:
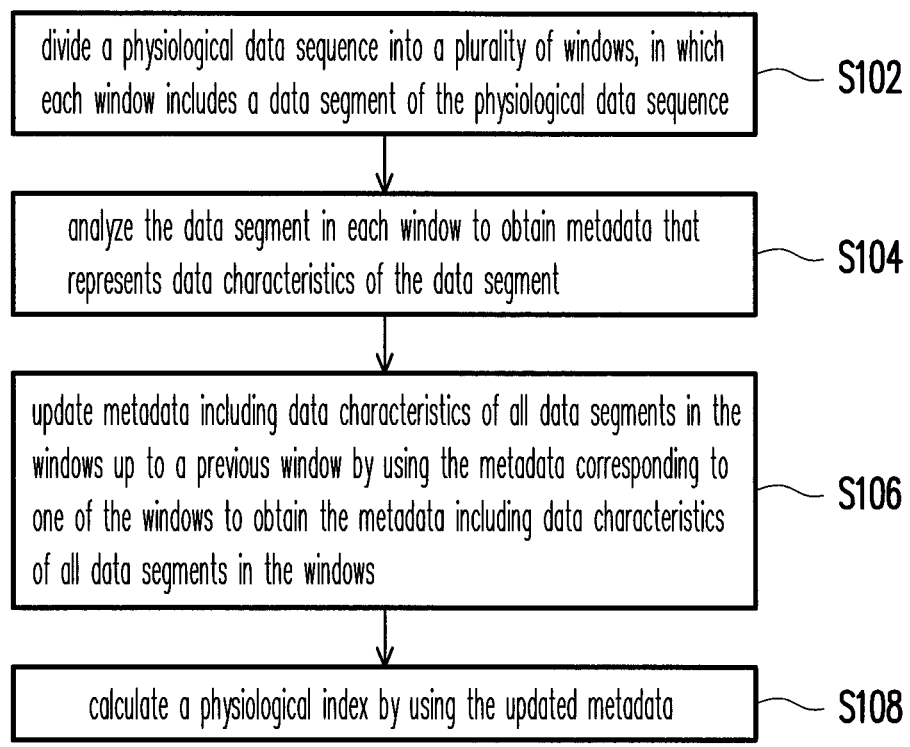
FIG. 1 is a flowchart of a method for calculating a physiological index according to an embodiment of the disclosure.

FIG. 1 is a flowchart of a method for calculating a physiological index according to an embodiment of the disclosure. Referring to FIG. 1, the calculation of a physiological index of this embodiment is applicable to various electronic devices with the calculation capability, and mainly includes division of a data sequence, calculation of metadata, accumulation and storage of metadata, and calculation of a physiological index, which are described as follows.

In Step S102, an electronic device receives a physiological data sequence that gradually enters the device, and divides the sequence into a plurality of windows, in which each window includes a data segment of the physiological data sequence. In particular, the division of the data sequence according to this embodiment includes, for example, sequences that represent each heartbeat cycle information such as R-R interval (RRI) and P-R interval (PRI) in an ECG signal are used to define a size of a window according to a fixed duration (for example, a half hour or an hour) or data length (for example, 5,000 RRI data points or 10,000 RRI data points). An original long-term data sequence (for example, a 24-hour RRI sequence) is divided into a plurality of non-overlapping data segments, so that the subsequent processing is to perform calculation on each data segment.

It should be noted that, the physiological data sequence is described by taking a data sequence of features of an ECG as example, and the features of the ECG include an R-R interval of adjacent heartbeats, a P-R interval in a single heartbeat, a QRS duration, an ST segment duration in an ECG measured from a temporal perspective, a delta of a P wave, an R wave, an S wave, and a T wave potential change between adjacent heartbeats measured from a spatial perspective, and a delta or a similarity of a pattern difference between adjacent ECGs measured from a morphological perspective. In addition to the data sequence of the features of an ECG record, the method of this embodiment is also used for other physiological data sequences, for example, features of a data sequence of an electroencephalogram record, a record of breathing signals or several kinds of oxygen saturation signals may also adopt the method of this embodiment to calculate a corresponding physiological index.

In Step S104, the electronic device analyzes the data segment in each window to obtain metadata that represents data characteristics of the data segment. In particular, according to the calculation property of the physiological index to be calculated, this embodiment can analyze metadata that is required for calculating the physiological index and the calculation manner, in which the metadata can be used to calculate the physiological index.

It should be noted that, the metadata is used to, for example, represent statistical descriptions of the data characteristics, data structure characteristics, trend information, or a data randomness measurement value. The statistical description includes a mean value, a standard deviation, a mode, a median, a coefficient of skewness, a coefficient of kurtosis, or parameters of probability distribution. The data structure characteristics include grouping or counting values of data histogram. The trend information includes a regression coefficient or a polynomial coefficient. The data randomness includes entropy or a temporal asymmetric index, which is not limited herein.

In Step S106, the electronic device updates metadata including the data characteristics of all data segments in the windows up to a previous window by using the metadata corresponding to one of the windows to obtain the metadata including the data characteristics of all data segments in the windows up to a current window. In particular, with the gradual entrance of data sequence into the system, this embodiment provides a metadata update method, so that the updated metadata can represent overall characteristics of the data sequences that have entered the system. It should be noted that, as for storage of the metadata, this embodiment particularly uses a multi-dimensional sparse matrix or tree data structure to record the metadata, and the specific implementation manner is described in detail in the following embodiments.

In Step S108, the electronic device calculates a physiological index by using the updated metadata. In particular, after the metadata of each time segment is updated, the updated metadata can be used to calculate the physiological index. As the metadata is different from the original physiological data sequence, the method for calculating the physiological index is also different from the conventional method. In order to calculate the physiological index, this embodiment provides additional data processing architecture for calculation, and the specific implementation manner is described in detail in the following embodiments.

Figure 2:
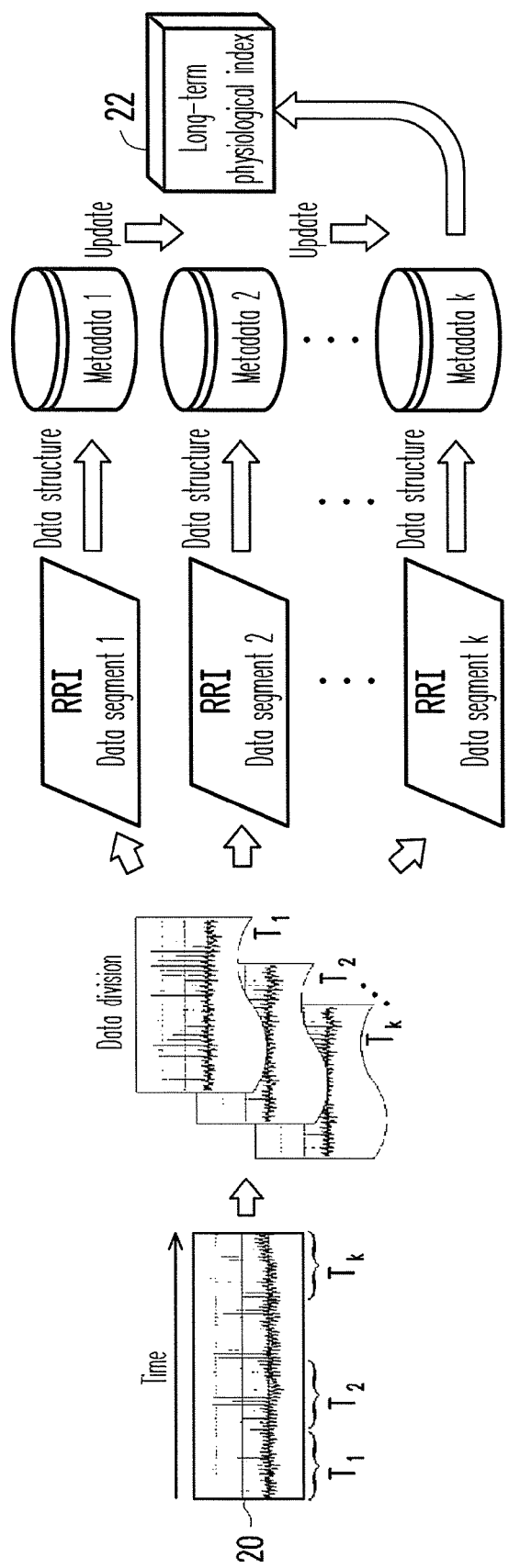
FIG. 2 is a diagram of a method for calculating a physiological index according to an embodiment of the disclosure.

FIG. 2 is a diagram of a method for calculating a physiological index according to an embodiment of the disclosure. Referring to FIG. 2, in this embodiment, a physiological data sequence 20 is divided into a plurality of short-duration data segments (including an RRI data segment 1, an RRI data segment 2, . . . , an RRI data segment k) according to a fixed duration ($T_1$, $T_2$, . . . , $T_k$). During analysis of the data segments, in this embodiment, a coarse-graining procedure in multi-scale analysis is first executed, and then metadata (including metadata 1, metadata 2, . . . , metadata k) that represents data characteristics of each data segment is calculated and stored by using a specific data structure. The metadata is gradually updated with each entered data segment to obtain the metadata that represents all long-term ECG characteristics, and finally, calculation of approximate entropy or sample entropy is performed, so as to obtain a desired long-term physiological index 22 and complete the calculation procedure of MSE.

It should be noted that, the coarse-graining procedure includes, for example, calculating the data segment in each window by using a plurality of scales respectively to obtain a data sequence under each scale, and using the data sequence to calculate metadata that represents data characteristics of the data segment. When executing the coarse-graining procedure on the data segment by using one of the scales, for example, with the used scale as a cell, a plurality of batches of data in the data segment is selected in sequence, and an average of the selected data is calculated and is used as a batch of data in the data sequence under the scale.

For example, FIG. 3(a) and FIG. 3(b) show examples of a coarse-graining procedure according to an embodiment of the disclosure. Referring to FIG. 3(a) and FIG. 3(b) together, as for a specified data sequence $X=\{x_i\}$, in which $1 \leq i \leq N$, a data sequence $v_j^{(\tau)}$ after performing the coarse-graining procedure on the data sequence X can be obtained through the following formula:

$$v_j^{(\tau)} = \frac{1}{\tau} \sum_{i=(j-1)\times\tau+1}^{j\times\tau} x_i, 1 \leq j \leq \frac{N}{\tau}.$$

In the formula, N is a total number of batches of data included in the data sequence X, $\tau$ is a selected coarse-graining scale. It can be known from FIG. 3(a) that, when scale $\tau=2$, that is, 2 batches of data in the data segment X is selected in sequence with 2 as a cell, for example, ($x_1$, $x_2$), ($x_3$, $x_4$), ($x_5$, $x_6$), . . . , $x_i$, $x_{i+1}$) . . . , and an average of the selected data is calculated and used as the data in the data sequence under the scale, so as to finally obtain a data sequence $V_\tau = V_2 = (v_1, v_2, v_3, \ldots)$ after the coarse-graining procedure. Similarly, it can be known form FIG. 3(b) that, when scale $\tau=3$, 3 batches of data in the data segment X is selected in sequence with 3 as a cell, and an average of the selected data is calculated and is used as the data in the data sequence under the scale, so as to finally obtain a data sequence $V3=(v_1', v_2', v_3', \ldots)$ after the coarse-graining procedure. Taking an actual number as an example, for an original data sequence X=(26, 28, 30, 26, 26, 27, 25), after the coarse-graining procedure ($\tau=2$) is performed, a data sequence $V_2$=(27, 28, 26.5) is obtained.

Figure 4:
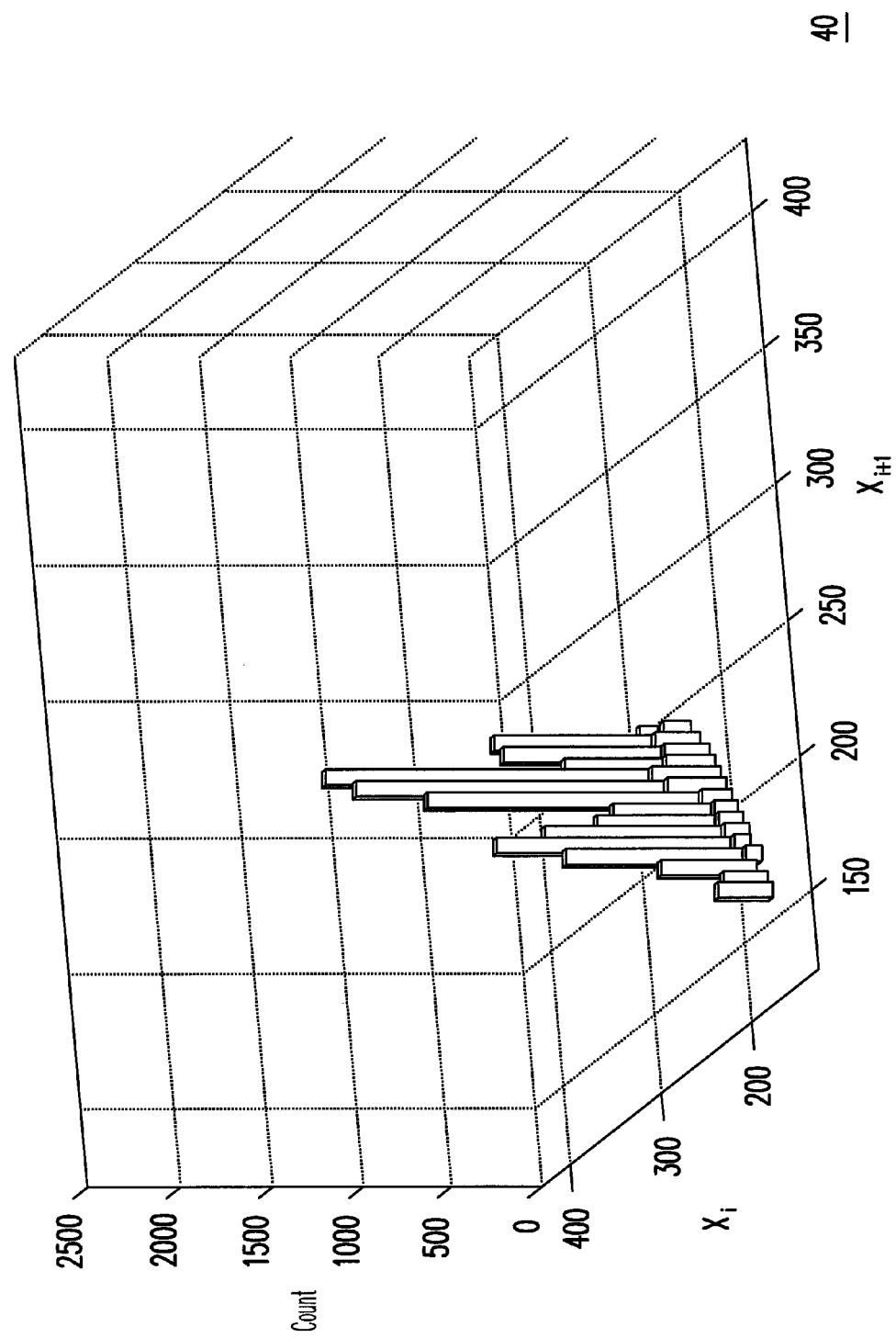
FIG. 4 is a histogram corresponding to a data structure for calculating MSE according to an embodiment of the disclosure.

As for the calculation and updating of the metadata, FIG. 4 is a histogram corresponding to a data structure for calculating MSE according to an embodiment of the disclosure. Referring to FIG. 4, histogram 40 is corresponding to a data structure that is used for calculating metadata deduced when the dimension of an observed sample is set to be m=2 in MSE according to this embodiment. As calculation of the approximate entropy or the sample entropy needs to compute statistics that can represent the relationship between each sample point and other sample points (for example, delta of a sample value), in this embodiment, multi-dimensional histogram process architecture is used to arrange the sample points (two-dimensional vector in this embodiment) according to the scale sample value, and the number of occurrences of each combination (two-dimensional vector) is calculated, thereby organized into a two-dimensional statistical table. When the dimension of observed sample is set to be m=3, the processing manner may be organized into a three-dimensional statistical table.

Although the number of sample points of the data segment entered each time may be up to several thousands/ten thousands, under the limitation of conditions of a first dimension sample value, the distributive scope of a second dimension sample value is extremely limited, this phenomenon is very reasonable for physical analysis of cardiac cycle, because the difference between two adjacent heartbeat cycle is not large. The phenomenon is more obvious in limiting a third dimension distribution (set to be m=3) under the first dimension and the second dimension sample value (that is, variation of the third dimension sample value is also limited).

According to the observed phenomenon, in a two-dimensional statistical table or a three-dimensional statistical table, the probability that each cell is valued is much lower than the probability that each cell is non-valued (that is, combination of the two dimensions or the three dimensions does not appear in the data). If it is intended to completely record the two-dimensional statistical table or the three-dimensional statistical table, it needs a lot of storage. Accordingly, a multi-dimensional sparse matrix may be used to record the statistical table.

In particular, as for the data sequence under each scale in each window divided from the physiological data sequence, in the embodiment of the disclosure, metadata corresponding to one window is recorded in a multi-dimensional sparse matrix, and then metadata corresponding to other windows is accumulated in sequence to the same multi-dimensional sparse matrix, so that the multi-dimensional sparse matrix includes metadata including data characteristics of all data segments up to a current window.

The step of recording the metadata includes, for example, first, recording a count of each vector combination included by the metadata corresponding to one window in a multi-dimensional sparse matrix, and then accumulating a count of each vector combination included by the metadata corresponding to the other windows in sequence to the count of the vector combination that is recorded in the multi-dimensional sparse matrix. The vector combination that is accumulated to the multi-dimensional sparse matrix may have different or the same parts with the original vector combination in the multi-dimensional sparse matrix. As for the same parts of the second vector combination and the first vector combination, the counts of the two combinations are accumulated; on the contrary, as for the different parts of the second vector combination and the first vector combination, no corresponding first vector combination exists in the multi-dimensional sparse matrix, so in the embodiment of the disclosure, as for the relative positions of all vector combinations in the multi-dimensional sparse matrix, the size of the multi-dimensional sparse matrix needs to be moderately expanded according to the second vector combination, so as to bring the second vector combination into the multi-dimensional sparse matrix and use the second vector combination as a newly added vector combination.

Figure 5:
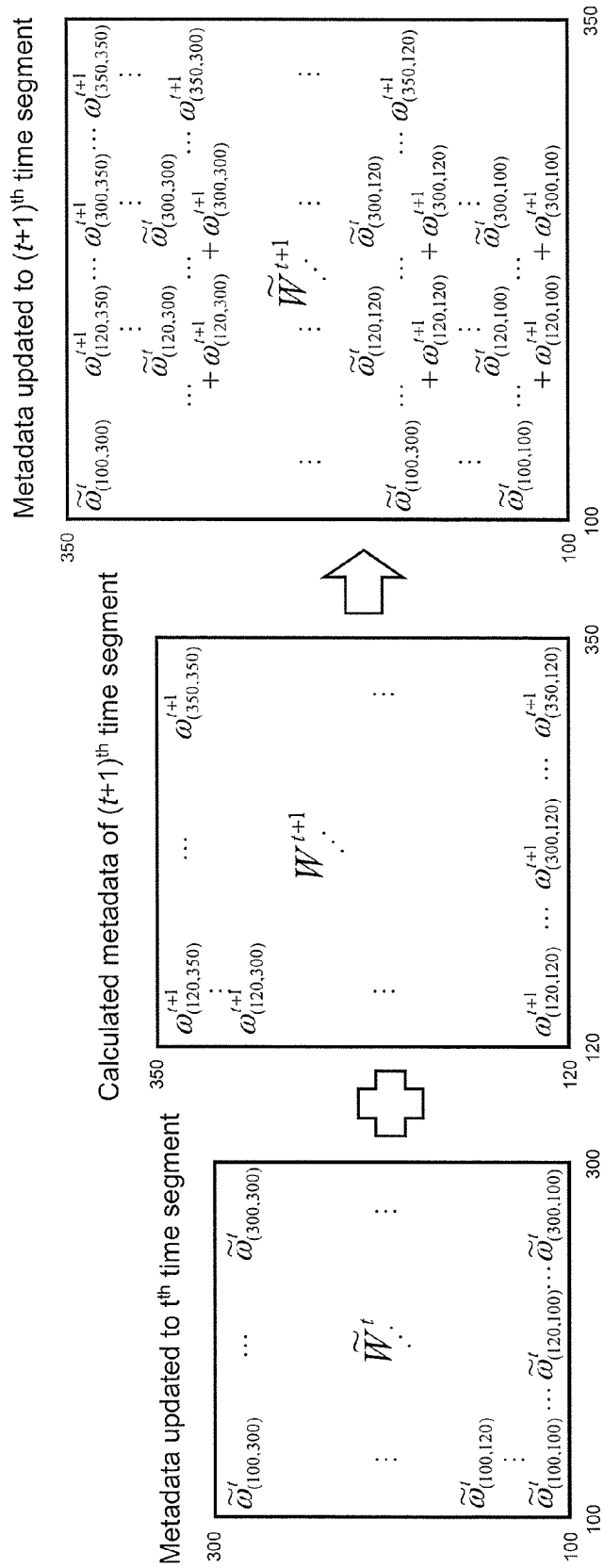
FIG. 5 shows an example of storing and updating metadata by using a sparse matrix according to an embodiment of the disclosure.

For example, FIG. 5 shows an example of storing and updating metadata by using a sparse matrix according to an embodiment of the disclosure. Referring to FIG. 5, this embodiment describes the recording and updating manner of metadata under the conditions that the scale for calculating the MSE is set to be m=2. It can be known from FIG. 5, in this embodiment, metadata (including information of previous t time segments) of a $t^{th}$ time segment (corresponding to a window t) recorded and updated in the multi-dimensional sparse matrix and metadata calculated by a $(t+1)^{th}$ time segment (corresponding to a window t+1) are converted into a full information matrix for metadata update, and the metadata in the information matrix after updating is recorded in a form of a multi-dimensional sparse matrix to serve as metadata updated to the $(t+1)^{th}$ time segment. In this way, the information matrix converted from the metadata continuously updates the information according to each data segment entered in the order of time, and the size of the information matrix may be expanded or remained unchanged in each updating process.

Figure 6:
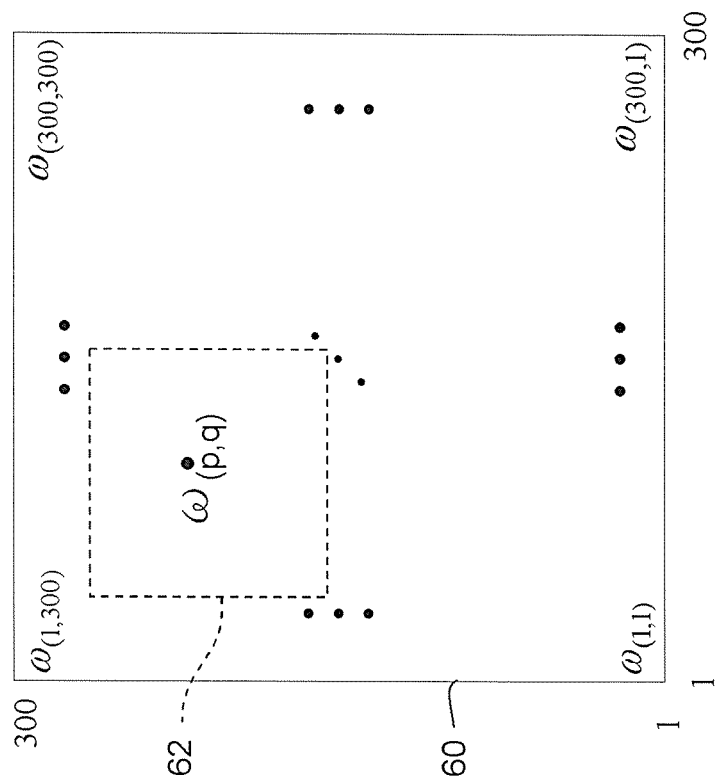
FIG. 6 is a schematic view of calculating MSE by using continuously updated metadata according to an embodiment of the disclosure.

FIG. 6 is a schematic view of calculating MSE by using continuously updated metadata according to an embodiment of the disclosure. Referring to FIG. 6, as statistics on the number of occurrences of each vector combination is continuously performed when the metadata is updated, in this embodiment, an information matrix 60 converted from the metadata sets that an upper bound of delta values defined in the MSE as r=0.15×SD, in which SD is a standard deviation of all RRI data up to a current time point. Accordingly, a block 62 that has a delta with a specific vector $\omega_{(p,q)}$ less than the upper bound r of delta values is enclosed, and the counts of all the vector combinations in the block 62 are added to obtain a count sum similar to the vector $\omega_{(p,q)}$. According to the number of occurrences of the target vector $\omega_{(p,q)}$ in the current accumulated data and total number of data in the range of r from the $\omega_{(p,q)}$, this motion is performed on each position in the information matrix 60 to obtain all information required for calculating the approximate entropy or the sample entropy. Multiple groups of data sequences under multiple scales are considered, and the operation is executed to calculate the MSE index.

Besides the method for recording the metadata by using a multi-dimensional sparse matrix, an embodiment of the disclosure further provides another method for recording the metadata by using a tree data structure.

In particular, for example, as for a data sequence under each scale of each window, metadata corresponding to one window is recorded in a tree data structure, and then metadata corresponding to other windows is added in sequence to this tree data structure, so that the tree data structure include metadata including data characteristics of all data segments up to a current window.

Figure 7:
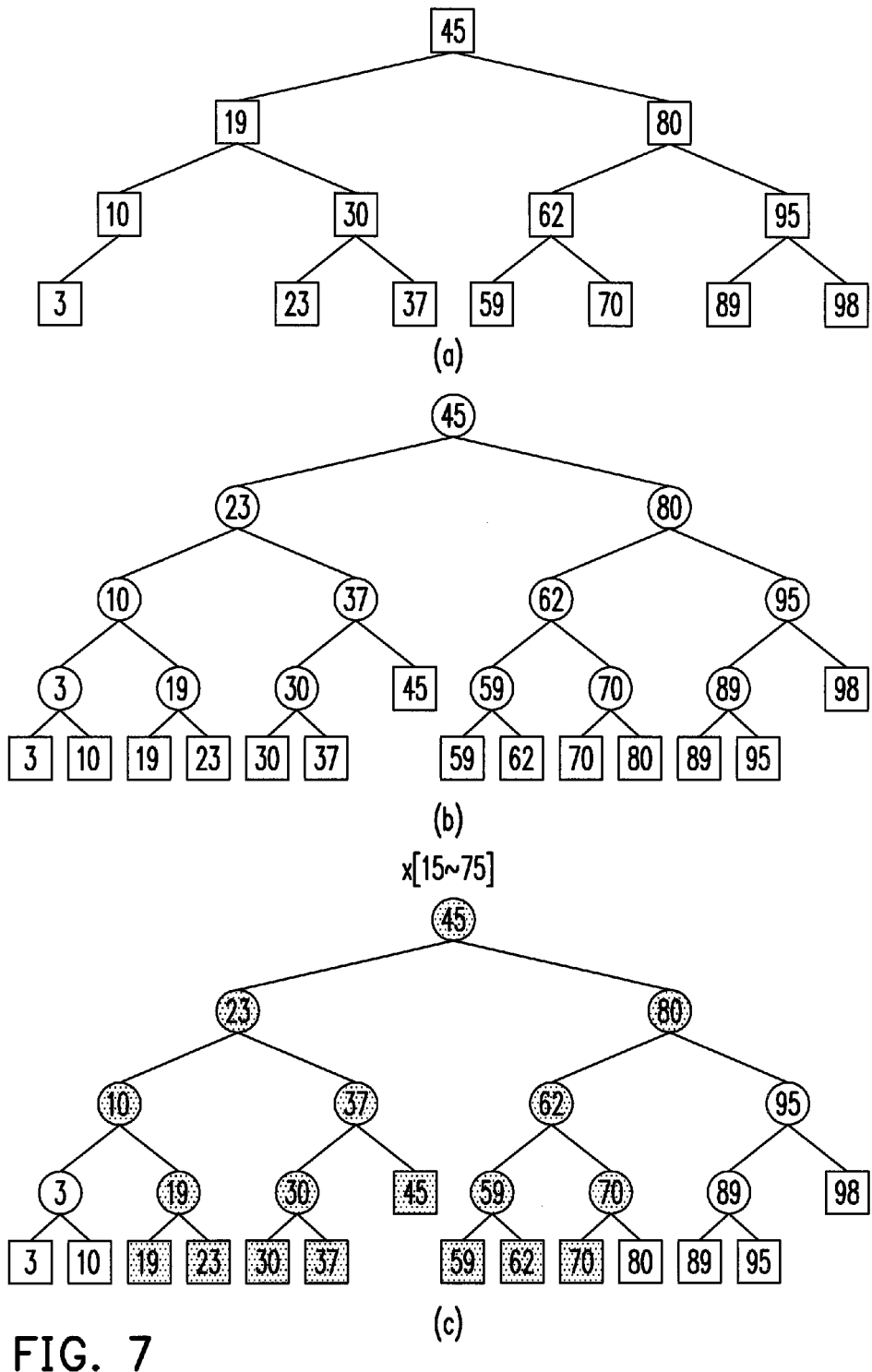
FIG. 7(a), FIG. 7(b), and FIG. 7(c) show examples of recording metadata by using a tree data structure and calculating a physiological index according to the metadata according to an embodiment of the disclosure.

For example, FIG. 7(a), FIG. 7(b), and FIG. 7(c) show examples of recording metadata by using a tree data structure and calculating a physiological index according to the metadata according to an embodiment of the disclosure. In this embodiment, a sample point in a data segment X=(3, 10, 19, 23, 30, 37, 45, 59, 62, 70, 80, 89, 95, 98) is recorded in a binary tree data structure (as shown in FIG. 7(a)) or in a 1D tree data structure (as shown in FIG. 7(b)). When a physiological index is calculated, an upper bound of delta values defined in the MSE is first set, and then as for a specific sample point in the tree data structure, a range in the tree data structure that has a delta with the sample point less than the upper bound of delta values is searched, and finally, a count sum of all vector combinations in the range is calculated to serve as information required for calculating a physiological index of approximate entropy/sample entropy. For example, in FIG. 7(c), the upper bound of delta values is set to be 30, as for the sample point x=45, a range (that is, x=15-75) in the tree data structure in FIG. 7(b) that has a delta with the sample point less than the upper bound of delta values is searched, and finally, a count sum of all vector combinations in the range is calculated to serve as information required for calculating a physiological index of approximate entropy/sample entropy.

Figure 8:
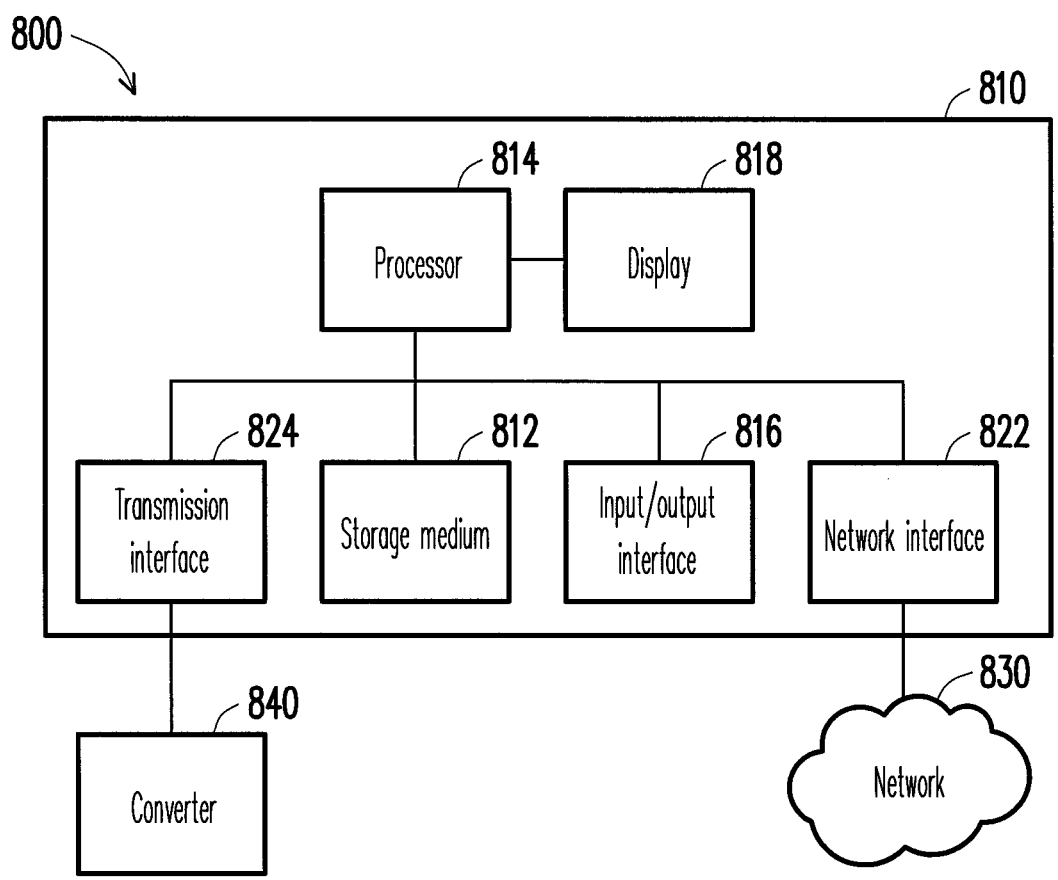
FIG. 8 is a function block diagram of a system for calculating a physiological index for executing the methods in FIG. 1 to FIG. 7 according to some embodiments.

According to some embodiments, FIG. 8 is a function block diagram of a system for calculating a physiological index for executing the methods in FIG. 1 to FIG. 7 according to some embodiment.

A system for calculating a physiological index 800 includes a computer system 810. The computer system 810 includes a processor 814 that is directly electrically connected to at least one storage medium 812. In order to enable a computer to execute calculation and analysis of a physiological index of a detected physiological signal, like a signal analyzer, a processor 814 is configured to execute or suspend a computer program code complied in the at least one storage medium 812.

In some embodiments, the processor 814 is a central processing unit (CPU), a multi-processor, a distributed processing system and/or a suitable processing unit. In at least one embodiment, the processor 814 may obtain a physiological signal such as an ECG signal, a predetermined standard template and/or other information from the at least one storage medium 812.

In some embodiments, the at least one storage medium 812 is an electronic, magnetic, optical, electromagnetic, infrared, and/or semiconductor system (instrument or device). For example, the at least one storage medium 812 includes a semiconductor or solid-state memory, a magnetic tape, a portable computer disk, a random access memory (RAM), a read-only memory (ROM), a hard disk and/or an optical disk. In some embodiments that an optical disk is used, the at least one storage medium 812 includes a compact disc read-only memory (CD-ROM), a compact disc rewritable (CD-RW) and/or a digital video disk (DVD).

Additionally, the computer system 810 includes an input/output interface 816 and a display 818. The input/output interface 816 and the processor 814 are directly connected. In order to execute the methods described in FIG. 1 to FIG. 7, an operator or a health care professional may be allowed to operate the computer system 810. The operating conditions of the methods described in FIG. 1 to FIG. 7 can be shown in the display 818 through a graphical user interface (GUI). The input/output interface 816 and the display 818 allow an operator to operate the computer system 810 in the manner of man-machine interaction.

In an embodiment, the computer system 810 may also include a network interface 822 that is directly connected to the processor 814. The network interface 822 allows the computer system 810 to communicate with one or more computer systems connected to a network 830. The network interface 822 includes a wireless network interface such as BLUETOOTH, wireless fidelity (WIFI), worldwide interoperability for microwave access (WiMAX), general packet radio service (GPRS), and wide band code division multiple access (WCDMA); and a wired network interface such as ETHERNET, universal sequence bus (USB) or IEEE-1394. In some embodiments, the methods in FIG. 1 to FIG. 7 may be executed in two or more computer systems 810 in FIG. 8, for example, a physiological signal such as an ECG signal, a predetermined standard template and/or other information can be exchanged between different computer systems through the network 830.

In at least one embodiment, the system for calculating a physiological index 800 further includes a converter 840. The converter 840 is used for observing a detected organism individual/organ and converting movement of the organism individual/organ into a representative signal. In an embodiment of analyzing an ECG signal, the converter 840 is used for observing a detected heart and converting the movement of heart muscle into an ECG signal.

The computer system 810 further has a transmission interface 824 that is directly connected to the converter 840 and the processor 814. The transmission interface 824 can bridge the converter 840 and the processor 814, and can output the obtained periodic signal in a format of, for example, a discrete time signal. For example, if the converter 840 obtains an ECG signal, the transmission interface 824 receives the ECG signal from the converter 840, and outputs the ECG signal in the format of an ECG data array to the processor 814. In some embodiments, the converter 840 converts one of the following phenomena of organism individual into an electronic signal: heartbeat, respiration, ECG, brain waves, oxygen saturation, and other physiological signals.

In order to verify that the method for calculating a physiological index of the disclosure is superior to the prior art, in the disclosure, three different calculation methods are used to evaluate the time for calculating MSE, which includes an original method that MSE does not perform any data structure processing on data, the method of the disclosure that metadata is stored as an orderly data structure and MSE is directly calculated in a manner of structured batch processing, and the method of the disclosure of structured online calculation of MSE. In the method of online calculation of MSE, all time (including time for calculating and updating metadata in each time segment entered and time for calculating MSE) consumed in the whole calculation process and time for an operator to actually wait for the system to operate complete MSE (including calculation and updating of metadata and calculation of MSE for one time) are additionally evaluated and respectively represented as a structured online calculation method (for all) and a structure online calculation method (for reaction time). The physiological data sequence used in this embodiment is 24-h ECG data, which is RRI sequential data obtained through automatic R wave characteristic point detection and ectopic wave filtering and is manually corrected by a professional. In the following embodiments, in setting the window length, the physiological data that gradually enters the system is divided in the manner of fixed data quantity, and the size of data of each window (time segment) is set to be 10,000 batches.

Figure 9:
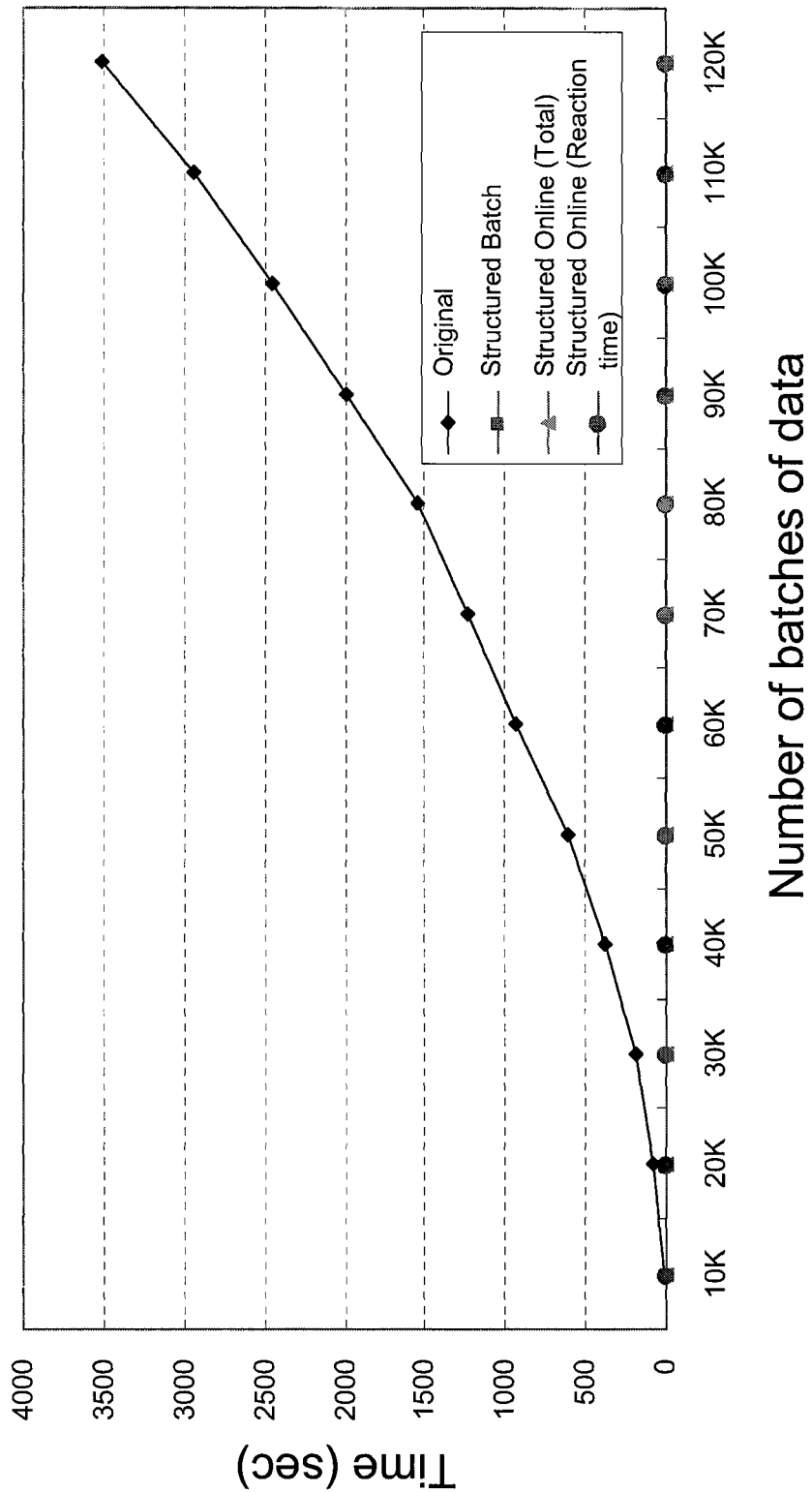
FIG. 9 is a time analysis chart of calculating MSE when a scale is set to be 1 by using four evaluation methods according to an embodiment of the disclosure.

FIG. 9 is a time analysis chart of calculating MSE when a scale is set to be 1 by using four evaluation methods according to an embodiment of the disclosure. It can be clearly seen from FIG. 9 that, the original brute force method without considering the data structure and computation efficiency is much poor than other evaluation methods in the performance of time efficiency, especially when the batches of data exceeds 30,000, the time required by the original brute force method is a hundredfold higher than the time required for other three evaluation methods. It can also be verified from FIG. 9 that, the calculation complexity of the original brute force method is increased with the increase in the number of batches of data by an exponential multiple.

Figure 10:
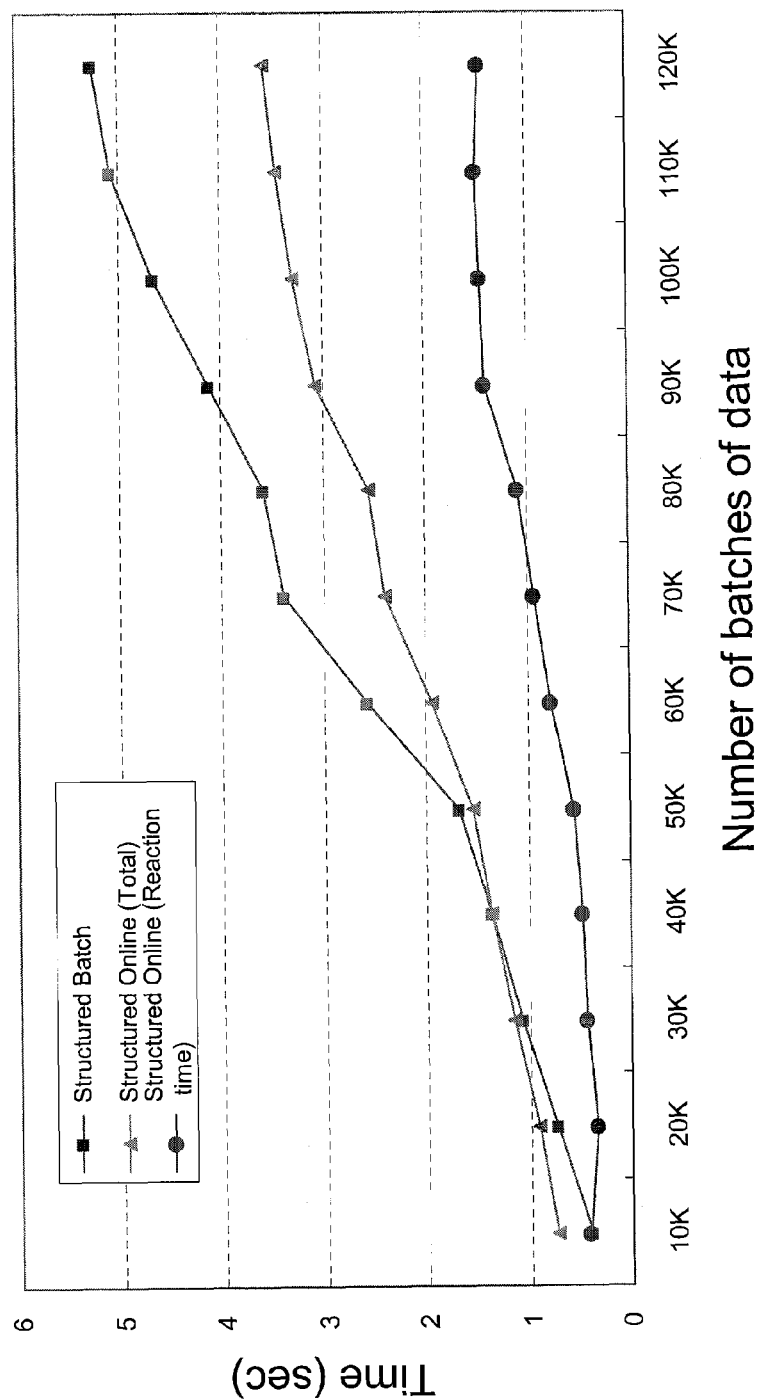
FIG. 10 shows comparison of calculating MSE by using a structured method according to an embodiment of the disclosure.

FIG. 10 shows comparison of calculating MSE by using a structured method according to an embodiment of the disclosure according to the experimental setting in FIG. 9. It can be found in FIG. 9 that, when the data quantity is less than 40,000, the structured batch calculation method is slightly more efficient than the structured online calculation method in terms of total calculation time, but when the number of batches of data is greater than 40,000, the structured online calculation (all) method is superior to the brute force methods in terms of computation efficiency; as compared with the structured online calculation (reaction time) method, the calculation time consumed by the structured online calculation method is extremely short, and when the number of batches of data is 120,000, merely 1.5 seconds are consumed, which is about a half of that of the structured online calculation method (for all) and about one third of that of the structured batch calculation method; and moreover, 1.5 seconds are the time that a clinical medical worker actually waits when operating and calculating the physiological index.

Figure 11:
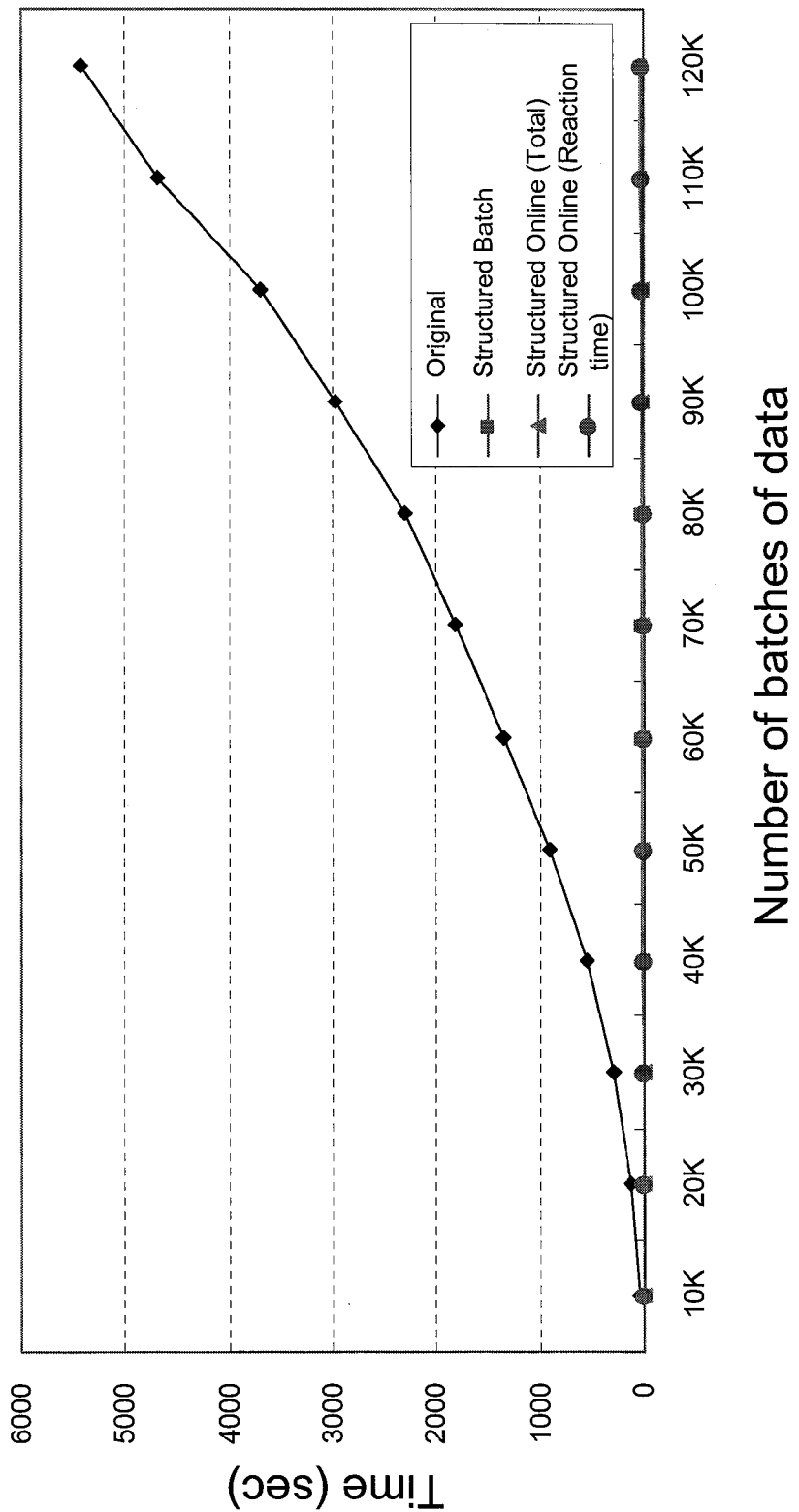
FIG. 11 is an analysis chart of total time consumed in calculating MSE when a scale is set to be 1 to 20 by using four evaluation methods according to an embodiment of the disclosure.

FIG. 11 is an analysis chart of total time consumed in calculating MSE when a scale is set to be 1 to 20 by using four evaluation methods according to an embodiment of the disclosure. Similar to the trend shown in FIG. 9, the calculation time of the brute force method is much longer than the time for calculating MES after the data is structured, and FIG. 11 can also explain why MSE has effects in research reports but fails to be popular. Taking the number of batches of data being 120,000 as an example, the original calculation method needs a calculation time of more than 5,000 seconds, thus leaving a large space for improvement as for real-time requirements in clinical evaluation applications.

Figure 12:
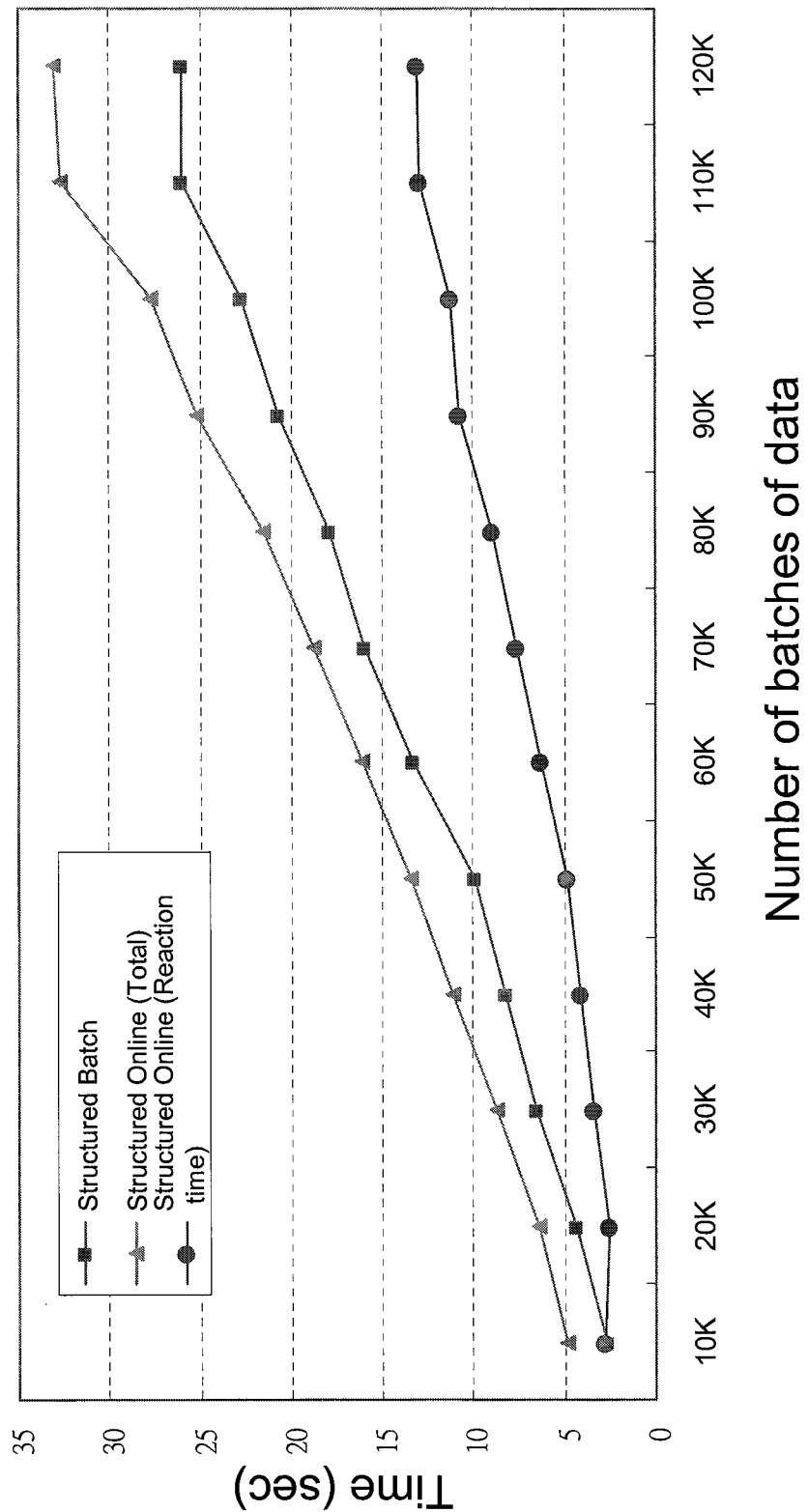
FIG. 12 shows analysis of time for calculating MSE by using a data structured method in FIG. 11.

FIG. 12 shows analysis of time for calculating MSE by using a data structured method in FIG. 11. The difference between the results in FIG. 9 and FIG. 10 lies in that, after the scales of 1 to 20 are considered, the total calculation time required by the structured online calculation method (for all) is higher than that of the brute force method, and the reason lies in that when the scale is greater than 3, the number of batches of data is greatly reduced after the physiological data is subjected to a coarse-graining procedure, and the processing efficiency of directly using the structured batch calculation method is higher than that of using the online method, because additional time for updating metadata is required in processing data of each window by using the online method, resulting in that the total calculation time is slightly higher than the time of the batch calculation method. As for the actual waiting time of clinical medical worker, the calculation time of the structured online calculation method (for reaction time) is similar to the result shown in FIG. 10, the structured online calculation method (for reaction time) is more efficient than the structured batch calculation method and the structured online calculation method (for all), and the calculation time is also merely a half of that required for the structured online calculation method (for all) and about one third of that required for the structured batch calculation method. The feasibility and computation efficiency of the method of the disclosure is also proved in the embodiment, through the online data process technology of sequential data learning, a long-term physiological index is provided.

It should be noted that, in an embodiment, besides the matrix structure and the tree structure are used to calculate and update the metadata, statistics of data probability distribution is further used as the metadata.

Figure 13A:
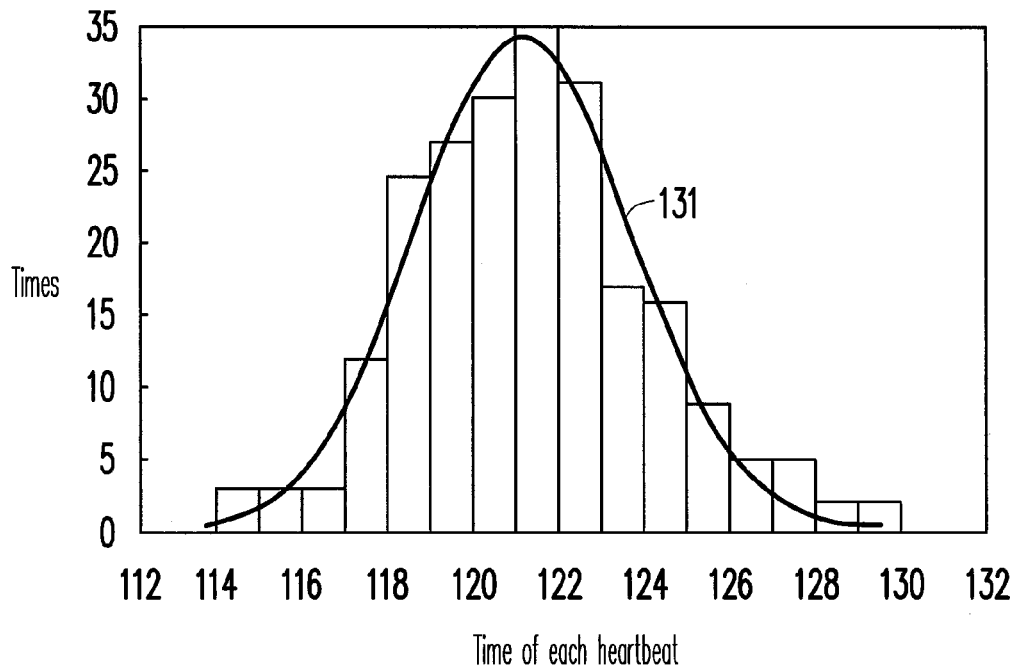
FIG. 13(a) and FIG. 13(b) show examples of recording metadata by using data distribution statistics and calculating a physiological index according to the metadata according to an embodiment of the disclosure.
Figure 13B:
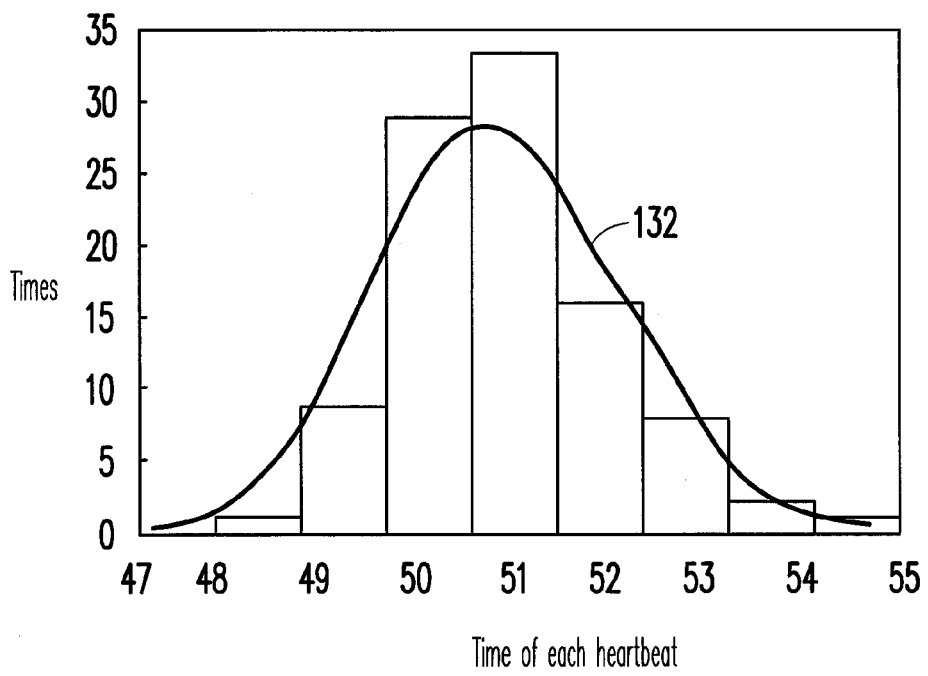

In particular, the probability distribution adopted in an embodiment of the present application is normal distribution, and the corresponding statistics is a mean value and a standard deviation. FIG. 13(a) and FIG. 13(b) show examples of recording metadata by using data distribution statistics and calculating a physiological index according to the metadata according to an embodiment of the disclosure. When the dimension m=2, in this embodiment, all two-dimensional sample points are arranged and organized according to the value, and a first dimension value of a sample point is fixed at a value, and a histogram plotted by using a second dimension value at the sample point is shown in FIG. 13(a). A curve 121 is a function graph of normal distribution, and it can be seen from FIG. 13(a) that, second dimension information generated by the normal distribution adopted in this embodiment when the first dimension is fixed is close to the distribution properties of the original data.

On the other hand, when the dimension m=3, the first dimension and the second dimension value of all three-dimensional sample points are fixed at a two dimension combination, a histogram of a third dimension information and corresponding normal distribution curve are shown in FIG. 13(b). Similarly, the extent that the normal distribution is close to the data characteristics can be seen from a curve 132 in FIG. 13(b).

After each window uses the distribution statistics as metadata, metadata updating may be performed with the distribution statistics of the subsequent windows, and an updating formula adopted in an embodiment is as follows:

$$\tilde{\mu}_{t+1} = (\tilde{N}_t \cdot \tilde{\mu}_t + N_{t+1} \cdot \mu_{t+1}) / (\tilde{N}_t + N_{t+1});$$

$$\tilde{\sigma}_{t+1} = \left[ \frac{\tilde{\sigma}_t^2 \cdot (\tilde{N}_t - 1) + \sigma_{t+1}^2 \cdot (N_{t+1} - 1) + \tilde{N}_t \cdot (\tilde{\mu}_t - \tilde{\mu}_{t+1})^2 + N_{t+1} \cdot (\mu_{t+1} - \tilde{\mu}_{t+1})^2}{\tilde{N}_t + N_{t+1} - 1} \right]^{1/2};$$

$$\tilde{N}_{t+1} = \tilde{N}_t + N_{t+1}$$

In the formula, $\tilde{N}_t$, $\tilde{\mu}_t$, $\tilde{\sigma}_t$ independently represent a number of samples and distribution statistics (including a mean value $\tilde{\mu}_t$ and a standard deviation $\tilde{\sigma}_t$) when being updated to a $t^{th}$ window; $N_{t+1}$, $\mu_{t+1}$, $\sigma_{t+1}$ represent a number of samples and distribution statistics calculated by a $(t+1)^{th}$ window; and $\tilde{N}_{t+1}$, $\tilde{\mu}_{t+1}$, $\tilde{\sigma}_{t+1}$ are a number of samples and distribution statistics when accumulated to the $(t+1)^{th}$ window after the two groups of metadata are updated. The finally recorded metadata and the final metadata obtained by using a sequential data learning method are completely identical with the metadata calculated by using the batch processing method.

After obtaining the metadata, in this embodiment, the distribution statistics may be standardized, in which a measure of area occupied by the standardized distribution function in each interval/region is multiplied by a number of samples having the first dimension equal to a predetermined value, a number of occurrences of each sample point (that is, vector combination) required for statistics when calculating MSE can be estimated.

Figure 14A:
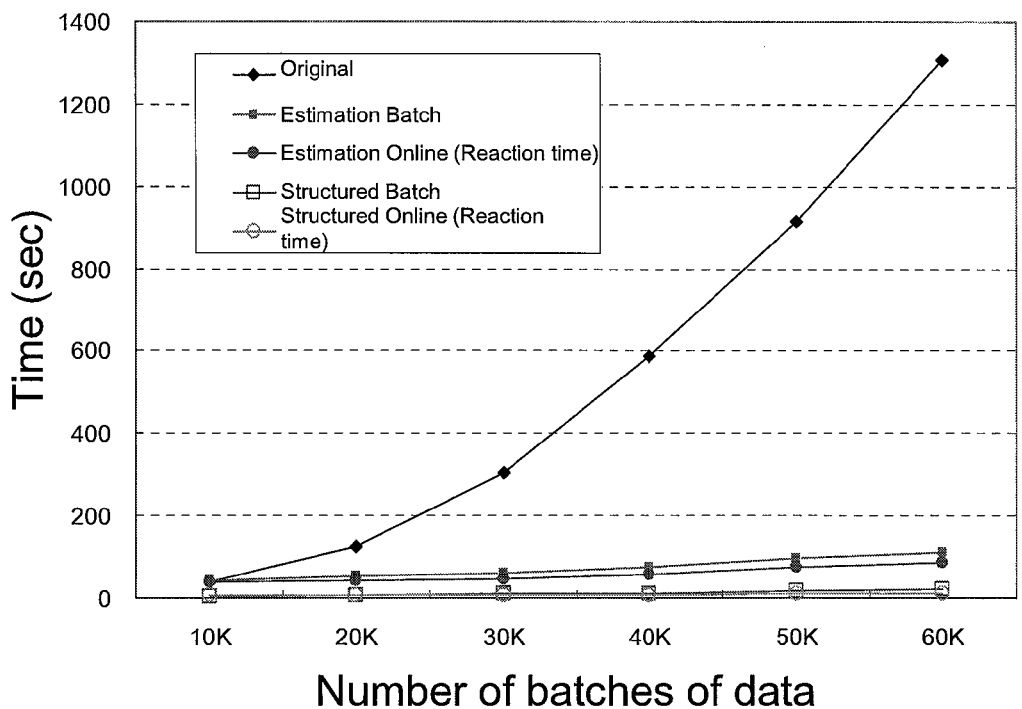
FIG. 14(a) and FIG. 14(b) are total time analysis charts of calculating MSE when a scale is set to be 1 to 20 by using five evaluation methods according to an embodiment of the disclosure.
Figure 14B:
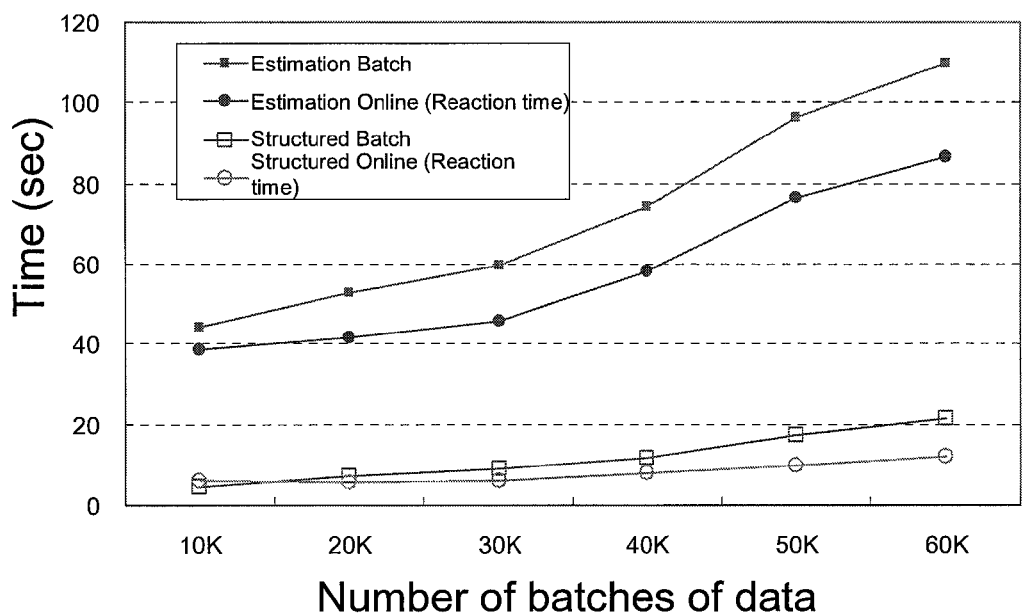

FIG. 14(a) and FIG. 14(b) are total time analysis charts of calculating MSE when a scale is set to be 1 to 20 by using five evaluation methods according to an embodiment of the disclosure. In order to verify that the method for calculating a physiological index of the disclosure is superior to the prior art, in this embodiment, the original calculation method, the structured batch calculation method, the structured online calculation method merely considering the structured online (for reaction time) of the final reaction time, the batch estimation method of the batch calculation distribution statistics, the online estimation (for reaction time) gradually calculating the distribution statistics and merely considering the final reaction time are compared.

It can be seen from FIG. 14(a), the calculation time consumed by the brute force method is in exponential growth, and is much higher than that of the four methods that uses the metadata for calculation. In the methods using the metadata, the method for calculating a physiological index by using the distribution statistics and the matrix structure to record the metadata is most efficient. When the number of batches of data is 60,000, the original calculation method needs to consume about 1,300 seconds, but it can be seen from details in FIG. 14(b) that, the batch calculation method using the distribution statistics merely needs to consume about 110 second, and the online estimation (for reaction time) using online estimation and merely considering the final reaction time merely needs 85 seconds, which is less than one tenth of that required by the original method. As for the calculation method using the matrix structure, the structured batch calculation method merely needs about 22 seconds, the time required for the structured online (for reaction time) is further reduced to 12 seconds, as compared with the brute force method, the efficiency of the two methods is improved by 50 times to 100 times. No matter the distribution statistics estimation or the matrix structure method is used to calculate MSE, adopting a gradually learning method can provide a physiological index, as compared with the batch method.

The disclosure may adopt online or batch processing.

An embodiment of the disclosure provides a computer readable recording medium with a stored program, which can complete the method when the program is loaded on a computer and is executed.

Based on aforesaid method and system, the application is able to process physiological data that is continuously input into the system. The application analyzes and processes the streaming of physiological data every preset time length or data amount instead of processing the whole physiological data after the physiological data is input into the system, and therefore the physiological data can be monitored and evaluated in real time.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method for calculating a physiological index, applicable to an electronic device, the method comprising:
   dividing a physiological data sequence into a plurality of windows, wherein each window comprises a data segment of the physiological data sequence;
   analyzing the data segment in each window to obtain metadata that represents data characteristics of the data segment;
   updating the metadata comprising the data characteristics of all data segments in the windows up to a previous window by using the metadata corresponding to one of the windows to obtain the metadata comprising the data characteristics of all data segments in the windows up to a current window; and calculating a physiological index by using the updated metadata, wherein the step of analyzing the data segment in each window to obtain the metadata that represents the data characteristics of the data segment comprises:

using a plurality of scales to perform a coarse-graining procedure on the data segment in each window to obtain a data sequence under the scales and using the data sequence as metadata that represents the characteristics of the data segment, wherein the step of updating the metadata comprising the data characteristics of all data segments in the windows up to the previous window by using the metadata corresponding to one of the windows to obtain the metadata comprising the data characteristics of all data segments in the windows up to the current window comprises:

as for the data sequence of each window under each scale, recording metadata corresponding to one of the windows by using a multi-dimensional sparse matrix; and cumulating metadata corresponding to other windows in sequence to the multi-dimensional sparse matrix, so that the multi-dimensional sparse matrix comprises the metadata comprising the data characteristics of all the data segments up to the current window.

2. The method for calculating a physiological index according to claim 1, wherein the step of dividing the physiological data sequence into the windows comprises:

defining a size of the windows according to a fixed duration or a data length; and dividing the physiological data sequence into a plurality of data segments that are not overlapped with each other according to the size of the windows.

3. The method for calculating a physiological index according to claim 1, wherein the step of using the plurality of scales to perform the coarse-graining procedure on the data segment in each window to obtain the data sequence under the scales comprises:

when using one of the scales to perform the coarse-graining procedure on the data segment, selecting a plurality of batches of data in the data segment in sequence in a cell of the scales, and calculating an average of the selected data to use the average as a batch of data in the data segment under the scale.

4. The method for calculating a physiological index according to claim 1, wherein as for the data sequence of each window under each scale, the step of recording the metadata corresponding to one of the windows by using the multi-dimensional sparse matrix comprises:

recording a first count of each first vector combination in a plurality of first vector combinations corresponding to the metadata in the multi-dimensional sparse matrix.

5. The method for calculating a physiological index according to claim 4, wherein the step of cumulating the metadata corresponding to the other windows in sequence to the multi-dimensional sparse matrix, so that the multi-dimensional sparse matrix comprises the metadata comprising the data characteristics of all the data segments up to the current window comprises:

cumulating a second count of each second vector combination in a plurality of second vector combinations of the metadata corresponding to the other windows in sequence to the counts of the first vector combinations recorded in the multi-dimensional sparse matrix.

6. The method for calculating a physiological index according to claim 4, wherein the step of calculating the physiological index by using the updated metadata comprises:

setting an upper bound of delta values defined in multi-scale entropy (MSE);

as for a specific vector combination in the multi-dimensional sparse matrix, enclosing a block in the multi-dimensional sparse matrix that has a delta with the specific vector combination less than the upper bound of delta values; and calculating a count sum of all vector combinations in the block to serve as information required for calculating the physiological index.

7. The method for calculating a physiological index according to claim 1, wherein the physiological data sequence comprises a data sequence of features of an electrocardiogram (ECG), features of electroencephalogram, a breathing signal or a oxygen saturation signals.

8. The method for calculating a physiological index according to claim 7, wherein the features of an ECG comprise an R-R interval of adjacent heartbeats, a P-R interval in a single heartbeat, a QRS duration, an ST segment duration in the ECG measured from a temporal perspective, a first delta of a P wave, an R wave, an S wave, and a T wave potential change between adjacent heartbeats measured from a spatial perspective, and a second delta or a similarity of a pattern difference between adjacent ECGs measured from a morphological perspective.

9. The method for calculating a physiological index according to claim 1, wherein the metadata comprises statistical descriptions, data structure characteristics, trend information, or a data randomness measurement for representing data characteristics.

10. The method for calculating a physiological index according to claim 9, wherein the statistical descriptions comprise a mean value, a standard deviation, a mode, a median, a coefficient of skewness, a coefficient of kurtosis, or parameters of probability distribution, the data structure characteristics comprises grouping or counting values of data histogram, the trend information comprises a regression coefficient or a polynomial coefficient, and the data randomness comprises entropy or a temporal asymmetric index.

11. A system for calculating a physiological index, comprising:

a converter, detecting a physiological data sequence; and a computer system, comprising:

a transmission interface, connected to the converter, receiving the physiological data sequence;

at least one non-transitory storage medium, storing the physiological data sequence; and a processor, coupled to the transmission interface and the at least one non-transitory storage medium, dividing the physiological data sequence into a plurality of windows, analyzing a data segment of the physiological data sequence in each window to obtain metadata that represents data characteristics of the data segment, updating metadata including the data characteristics of all data segments in the windows up to a previous window by using the metadata corresponding to one of the windows to obtain the metadata including data characteristics of all data segments in the windows up to a current window; and calculating a physiological index by using the updated metadata, wherein, for analyzing the data segment in each window to obtain the metadata that represents the data characteristics of the data segment, the processor is further configured for using a plurality of scales to perform a coarse-graining procedure on the data segment in each window to obtain a data sequence under the scales and using the data sequence as metadata that represents the characteristics of the data segment, wherein, for updating the metadata comprising the data characteristics of all data segments in the windows up to the previous window by using the metadata corresponding to one of the windows to obtain the metadata comprising the data characteristics of all data segments in the windows up to the current window, the processor is further configured for, as for the data sequence of each window under each scale, recording metadata corresponding to one of the windows by using a multi-dimensional sparse matrix, and cumulating metadata corresponding to other windows in sequence to the multi-dimensional sparse matrix, so that the multi-dimensional sparse matrix comprises the metadata comprising the data characteristics of all the data segments up to the current window.

12. The system for calculating a physiological index according to claim 11, further comprising:
a display, connected to the processor, displaying a graphical user interface for operating the computer system; and
an input/output interface, connected to the processor, receiving an operation of a user on the computer system.

13. The system for calculating a physiological index according to claim 11, further comprising:
a network interface, connected to the processor, communicating with other computer systems through a network.

14. A non-transitory computer readable recording medium for storing a program, capable of implementing the method according to any one of claims 1, 2, 3, 4 to 6 and 7 to 10 after the program is loaded on a computer and is executed.

* * * * *